(12) United States Patent
Marko

(10) Patent No.: US 7,186,557 B2
(45) Date of Patent: Mar. 6, 2007

(54) METHODS OF PRODUCING NEURONS

(75) Inventor: Olga Marko, Houston, TX (US)

(73) Assignee: Isolagen Technologies, Inc., Houston, TX (US)

( * ) Notice: Subject to any disclaimer, the term of this patent is extended or adjusted under 35 U.S.C. 154(b) by 108 days.

(21) Appl. No.: 10/461,795

(22) Filed: Jun. 13, 2003

(65) Prior Publication Data

US 2004/0253718 A1 Dec. 16, 2004

(51) Int. Cl.
*C12N 5/00* (2006.01)
*C12N 5/02* (2006.01)
(52) U.S. Cl. .................. 435/377; 435/325; 435/388
(58) Field of Classification Search .................. None
See application file for complete search history.

(56) References Cited

U.S. PATENT DOCUMENTS 5,858,390 A * 1/1999 Boss, Jr. .................. 424/426
6,787,355 B1 * 9/2004 Miller et al. .............. 435/377

OTHER PUBLICATIONS

E. Buse, "Development of Serotoninergic Neurons From Ventricular Cells of the Mouse Neural Plate *In Vitro*", Int. J. Devl. Neuroscience, 5(2):107-115, (1987).

* cited by examiner

*Primary Examiner*—David S Romeo
*Assistant Examiner*—Daniel C Gamett
(74) *Attorney, Agent, or Firm*—Fish & Richardson P.C.

(57) ABSTRACT

The invention provides a method of producing neurons from undifferentiated mesenchymal cells (UMC). Also featured by the invention is an isolated neuron produced by this method, compositions containing such neurons, and a method of repairing damaged or defective neural tissues using such compositions.

14 Claims, No Drawings

METHODS OF PRODUCING NEURONS

TECHNICAL FIELD

This invention relates to the production of cellular compositions, and more particularly to compositions containing neurons.

BACKGROUND

In light of the inefficiency and slowness of neural tissue healing, there is a pressing need to develop methods of producing transplantable or implantable compositions of neurons. Naturally, as in all organ, tissue, or cell transplantation, it is crucial that immunological rejection of neuron grafts be avoided.

SUMMARY

The inventor has discovered that culturing of undifferentiated mesenchymal cells (UMC) in plasma clots results in the outgrowth of neurons in the plasma clots. Thus, the invention features a method of producing a population of neurons that involves culturing UMC in a plasma clot. The invention also provides an isolated neuron produced by such a method and a composition containing an isolated population of cells that includes neurons made by the method of the invention. In another embodiment, the invention includes a method of repairing a neural tissue defect or damage to neural tissue.

More specifically, the invention features a method of producing neurons. The method involves the sequential steps of: (a) providing a source of undifferentiated mesenchymal cells (UMC); (b) providing a plasma clot containing about 6 mM to about 18 mM $Ca^{2+}$; (b) incorporating UMC from the source into the plasma clot; and (c) incubating the plasma clot. During the incubation, a subpopulation of the UMC in the plasma clot differentiates into neurons, thereby creating in the plasma clot a population of cells comprising neurons. The method can further involve isolating the population of cells from the plasma clot and, optionally, culturing the isolated population of cells in a serum-free culture medium.

The source of UMC can optionally have been obtained from an individual to whom the population is administered. The source of UMC can be, for example, a fragment of mammalian skin or a fragment of mammalian fat tissue.

Moreover, the source of UMC can be a population of non-adherent derivative cells containing UMC, the non-adherent derivative cells being produced by a process that includes the steps of: (a) providing a fragment of undifferentiated mesenchymal cell (UMC)-containing tissue to obtain starting cells; (b) separating the starting cells from the fragment; (c) culturing the starting cells; and d) harvesting a population of non-adherent derivative cells from the culture, the non-adherent derivative cells containing UMC. The process of producing a population of cells containing UMC can further include one or more rounds of derivitization involving repeating steps (c) and (d) utilizing the harvested population of non-adherent derivative cells from the previous round as the starting cells. The one or more additional rounds of derivatization can be from one to twenty rounds. The UMC-containing tissue can be, without limitation, dermal tissue, adipose tissue, connective tissue, fascia, lamina propria, or bone marrow. The process can further include culturing the non-adherent cells in the presence of acidic fibroblast growth factor.

The invention also provides: (i) a neuron produced by the above method; and (ii) a cell population that includes neurons, the cell population having been produced by the above method. The composition can further contain a pharmaceutically acceptable carrier, and/or an acellular biodegradable matrix wherein cells of the cell population are integrated in or on the matrix, and/or an acellular biodegradable filler. The acellular biodegradable matrices and acellular biodegradable fillers, prior to combination with cells, are composed of any of the substances, or combinations of substances, recited herein as useful for acellular biodegradable matrices and acellular biodegradable fillers. In addition, the composition can be substantially free of culture medium serum-derived proteins.

Another aspect of the invention is a method of repairing damaged or defective neural tissue in a mammalian subject. The method involves injecting into, grafting to, or implanting in, the neural tissue the composition of the invention. The neural tissue can be a central nervous system (CNS) tissue, e.g., spinal cord tissue or brain tissue. The neural tissue can also be peripheral nervous system (PNS) tissue. The mammalian subject can be a human patient The mammalian subject can have a spinal chord injury or a disease or defect such as Alzheimer's Disease, Parkinson's Disease, Huntington's Disease, Tay-Sachs Disease, amylotrophic lateral sclerosis, stroke, facial nerve degeneration, peripheral injury of hands, neurofibromatosis, fibromyalgia, syringomyelia, an autoimmune diseases of the nervous system, and a neural tissue tumor. In this method, the cell population of the composition can be autologous.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and from the claims.

DETAILED DESCRIPTION

The invention provides an method of generating neurons in vitro from undifferentiated mesenchymal cells (UMC). These neurons can be used to treat defects or damaged neural tissue of a variety of types, e.g., tissue of the central nervous system (CNS) (e.g., spinal cord or brain) or the peripheral nervous system (PNS) (e.g., the sensory-somatic nervous system (e.g., cranial nerves or spinal nerves) or the autonomic nervous system). Thus, compositions containing neurons generated by the method of the invention can be used for the treatment of, for example, spinal injuries, Alzheimer's Disease, Parkinson's Disease, Huntington's Disease, Tay-Sachs Disease, amylotrophic lateral sclerosis, stroke including muscle paralysis from stroke, facial nerve degeneration, peripheral injury of hands, neurofibromatosis, fibromyalgia, syringomyelia, autoimmune diseases of the nervous system (e.g., multiple sclerosis), and malignant or benign neural tissue tumors (e.g., astrocytomas or glioblastoma), e.g., as replacement therapy following surgical removal of such a tumor.

The UMC and neurons derived from them share at least one major histocompatibility complex (MHC; HLA in humans) haplotype with the recipient of the neurons. The donor of the UMC and the recipient of the neurons are preferably MHC identical. Optimally, the recipient and the donor are homozygotic twins or are the same indvidual. Where biological components (e.g., tissues, cells, or biological molecules such as proteins, nucleic acids, carbohydrates, or lipids) are to be transplanted or implanted into a recipient from which they were obtained, or from which precursors of the biological components were obtained, the biological components are referred to herein as "autologous."

Methods of Making Compositions Containing Neurons

Undifferentiated Mesenchymal Cells

As used herein, the term "UMC" refers to cells that are at a "stage" of differentiation prior to fully differentiated connective tissue cells such as, for example, fibroblasts. Because UMC cannot differentiate into every type of somatic cell, UMC are different from pluripotent stem cells. In addition to fibroblasts, UMC can differentiate into adipose tissue, cartilage, tendon, bone, muscle cells, and neurons. While neurons are not considered mesenchymal tissue, clearly neurons can be produced from UMC. The mechanism by which this occurs is not clear. One possibility is that precursor cells apparently committed to a particular differentiative pathway (e.g., UMC) are not as limited with respect to the range of fully differentiated cells into which they can develop as was previously thought; for example, it is known that neural crest cells can develop into not only neurons but also, e.g., support cells of the PNS, pigment cells, smooth muscle cells, cartilage and bones of the face and skull. Alternatively, it is possible that at least some partially differentiated cell types (e.g., UMC) are capable, under certain circumstances (e.g., those occurring in a plasma clot) of dedifferentiating and then redifferentiating along a different (e.g., a neural) pathway. The invention is not limited by any particular mechanism of neuron development from UMC.

The methods of the invention involve growing of neurons in plasma clots using as a source of the neuron precursor cells essentially any source of UMC. The UMC can be in fresh tissue (e.g., skin, fat (adipose) tissue, or bone marrow) that has not been previously cultured or the UMC can have been grown and/or enriched in vitro by any of a variety of methods known in the art, e.g., those in Example 1. The culturing in the plasma clots results in: (a) either selective outgrowth of already differentiated neurons in the UMC populations and having, prior to the culture in the plasma clot, the same morphology as the UMC; or (b) differentiation from a subset of UMC into, followed by growth of, neurons. The invention is not limited by any particular mechanism of action.

The UMC can be obtained from any of a wide range of mammalian species, e.g., humans, non-human primates (e.g., monkey, chimpanzees, and baboons), cows, sheep, horses, goats, pigs, dogs, cats, rabbits, guinea pigs, hamsters, gerbils, rats, or mice.

UMC can be harvested and enriched in vitro by initiation of cultures from biopsies taken from a subject (e.g., a human). As described herein, UMC can be obtained from, for example, a skin biopsy or a biopsy of adipose tissue or bone marrow. UMC isolated from dermal tissue are particularly useful because they can be readily obtained and expanded.

To generate in vitro selected UMC useful for the invention, a culture can be initiated from, for example, a full thickness (e.g., 1–5 mm, or more than 5 mm if enough tissue is available) dermal biopsy specimen of the gums, scalp skin, post-auriculum skin, or the palate of a subject. The dermis is located just beneath the epidermis, and typically has a thickness that ranges from 0.5 to 3 mm. A dermal specimen can be obtained using, for example, a punch biopsy procedure. Skin biopsies can be taken from skin that is located, for example, behind the ear. Before initiation of the cell culture, a biopsy can be washed repeatedly with antibiotic and antifungal agents in order to reduce the potential for contamination of subsequence cultures. A suitable "wash medium" can contain, for example, a tissue culture medium such as Dulbecco's Modified Eagle's Medium (DMEM), Iscove's Modified Dulbecco's Medium (IMDM), or any suitable culture medium, along with some or all of the following antibiotics: gentamicin, amphotericin B (FUNGIZONE®), Mycoplasma removal agent (MRA; Dianippon Pharmaceutical Company, Japan), plasmocin, and tylosin (available from, for example, Serva, Heidelberg, Germany). Gentamicin can be used at a concentration of 10 to 100 µg/ml (e.g., 25 to 75 µg/ml, or about 50 µg/ml). Amphotericin B can be used at a concentration of 0.5 to 12.5 µg/ml (e.g., 1.0 to 10.0 µg/ml, or about 2.5 µg/ml). MRA can be used at a concentration of 0.1 to 1.5 µg/ml (e.g., 0.25 to 1.0 µg/ml, or about 0.5 µg/ml). Plasmocin can be used at a concentration of 1 to 50 µg/ml (e.g., 10 to 40 µg/ml, or about 25 µg/ml). Tylosin can be used at a concentration of 0.012 to 1.2 mg/ml (e.g., 0.06 to 0.6 mg/ml, or about 0.12 mg/ml).

If desired, sterile microscopic dissection can be used to separate dermal tissue in a biopsy from keratinized tissue-containing epidermis and from adipocyte-containing subcutaneous tissue. The biopsy specimen then can be separated into small pieces using, for example, a scalpel or scissors to finely mince the tissue. In some embodiments, the small pieces of tissue are digested with a protease (e.g., collagenase, trypsin, chymotrypsin, papain, or chymopapain). Digestion with 200–1000 U/ml of collagenase type II for 10 minutes to 24 hours is particularly useful, although any type of collagenase can be used (e.g., 0.05% to 0.1% collagenase type IV can be particularly useful for digestion of fat tissue). If enzymatic digestion is used, cells can be collected by centrifugation and plated in tissue culture flasks.

If the tissue is not subjected to enzymatic digestion, minced tissue pieces can be individually placed onto the dry surface of a tissue culture flask and allowed to attach for between about 2 and about 10 minutes. A small amount of medium can be slowly added so as not to displace the attached tissue fragments. In the case of digested cells, the cells can be washed with culture medium to remove residual enzyme, suspended in fresh medium, and placed in one or more flasks. After about 48–72 hours of incubation, flasks can be fed with additional medium. When a T-25 flask is used to start the culture, the initial amount of medium typically is about 1.5–2.0 ml. The establishment of a cell line from the biopsy specimen can take between about 2 and 3 weeks, at which time the cells can be removed from the initial culture vessel for expansion.

During the early stages of the culture, it is desirable that the tissue fragments remain attached to the culture vessel bottom. Fragments that detach can be reimplanted into new vessels. The cells can be stimulated to grow by a brief exposure to EDTA-trypsin, according to standard techniques. Such exposure to trypsin is too brief to release the fibroblasts from their attachment to the culture vessel wall. Immediately after the cultures become established and are approaching confluence, samples of the cells can be processed for frozen storage in, for example, liquid $N_2$ (see below for additional information on cell freezing). As used herein, "adherent" cells are cells that adhere to the material (e.g., plastic) of a standard tissue culture vessel. As used herein, "non-adherent" cells include cells that do not adhere to the material (e.g., plastic) of a standard tissue culture vessel, as well as cells that detach from the surface of a tissue culture vessel when space and nutrients become limiting.

Once the cells have reached confluent or almost confluent conditions, non-adherent colonies of actively growing UMC can be observed floating in the above-described cultures. While the invention is not limited by any particular mechanism of action, it is possible that the initially adherent UMC detach (i.e., become non-adherent) because of space and./or nutrient limitations. These colonies of non-adherent UMC can be harvested by aspiration and centrifugation of culture medium from the cell culture, and can be either used (e.g., for making neurons), frozen and stored, or expanded by reseeding into fresh tissue culture medium. On reseeding of the non-adherent colonies in a fresh tissue culture vessels, the cells again adhere to the floor and/or walls of the tissue culture vessel and acquire a cobblestone-like morphology. The process of cell growth, and harvesting and reseeding of non-adherent colonies can be repeated as often as desired. It can be carried out, for example, only once or two, three, four, five, six, seven, eight, nine, ten, 12, 15, 17, 20, 25, 30, 35, 40, 45, 50, 60, 70, 80, 90, 100, 200, 500, 1000 or even more times.

Non-adherent UMC also can also be isolated from cultures of adipose tissue (e.g., fat harvested by liposuction or other surgical removal). The tissue can be cut into small pieces, membranous material can be removed, and the resulting tissue can be placed in culture under conditions that lead to active shedding of UMC from the adipose tissue. Alternatively, the adipose tissue can be dissociated with about 0.1% to 1% collagenase after removal of membranes from the fat globules. Similarly, UMC cultures can be initiated from biopsies of bone marrow (see, e.g., Marko et al. (1995) *Endocrinol.* 136:4582–4588). The harvesting and reseeding process is the same for fat- and bone marrow-derived UMC as that described above for skin-derived UMC. Indeed, one of skill in the art will appreciate that analogous procedures can be performed to obtain UMC from any tissue disclosed herein as a potential source of UMC.

The invention includes an isolated UMC neuron precursor cell derived by the above-described culture methodology and compositions containing cell populations derived by the above-described culture methodology and which include precursor cells of neurons.

Any tissue culture technique that is suitable for the propagation of UMC from biopsy specimens can be used to expand the cells. Useful techniques for expanding cultured cells can be found in, for example, R. I. Freshney, Ed., *Animal Cell Culture: A Practical Approach*, (IRL Press, Oxford, England, 1986) and R. I. Freshney, Ed., *Culture of Animal Cells: A Manual of Basic Techniques*, (Alan R. Liss & Co., New York, 1987).

Cell culture medium can be any medium suitable for the growth of primary UMC cultures. Culture medium can contain antibiotics, antimycotics, and/or reagents that prevent the growth of mycoplasma, as described above. The presence of, for example, acidic fibroblast growth factor (aFGF) in the culture medium can prevent the UMC from differentiating into fibroblasts. The medium can be serum-free, or can be supplemented with human or non-human serum [e.g., autologous human serum, non-autologous human blood group A/B serum, non-autologous human blood group O serum, horse serum, or fetal bovine serum (FBS)] to promote growth of the cells. When included in the medium, serum typically is in an amount between about 0.1% and about 20% v/v (e.g., between about 0.5% and about 19%, between about 1% and about 15%, between about 5% and about 12%, or about 10%). A particularly useful medium contains glucose DMEM that is supplemented with about 2 mM glutamine, about 10 mg/L sodium pyruvate, about 10% (v/v) FBS, and antibiotics (often called "complete medium"), wherein the concentration of glucose ranges from about 1,000 mg/L to about 4,500 mg/L. UMC also can be expanded in serum-free medium; in this way, the UMC are never exposed to xenogeneic or allogeneic serum proteins and do not require the extra culturing in serum-free medium that is carried out when the cells are expanded in medium that contains non-autologous serum.

Medium used for cell culture can be supplemented with antibiotics to prevent contamination of the cells by, for example, bacteria, fungus, yeast, and mycoplasma. Mycoplasma contamination is a frequent and particularly vexatious problem in tissue culture. In order to prevent or minimize mycoplasma contamination, an agent such as tylosin can be added to the culture medium. The medium can be further supplemented with one or more antibiotics/antimycotics (e.g., gentamicin, ciprofloxacine, alatrofloxacine, azithromycin, MRA, plasmocin, and tetracycline). Tylosin can be used at a concentration of 0.006 to 0.6 mg/ml (e.g., 0.01 to 0.1 mg/ml, or about 0.06 mg/ml). Gentamicin can be used at a concentration of 0.01 to 0.1 mg/ml (e.g., 0.03 to 0.08 mg/ml, or about 0.05 mg/ml). Ciprofloxacine can be used at a concentration of 0.002 to 0.05 mg/ml (e.g., 0.005 to 0.03 mg/ml, or about 0.01 mg/ml). Alatrofloxacine can be used at a concentration of 0.2 to 5.0 µg/ml (e.g., 0.5 to 3.0 µg/ml, or about 1.0 µg/ml). Azithromycin can be used at a concentration of 0.002 to 0.05 mg/ml (e.g., 0.005 to 0.03 mg/ml, or about 0.01 mg/ml). MRA can be used at a concentration of 0.1 to 1.5 µg/ml (e.g., 0.2 to 1.0 µg/ml, or about 0.75 µg/ml). Plasmocin can be used at a concentration of 1 to 50 µg/ml (e.g., 10 to 40 µg/ml, or about 25 µg/ml). Tetracycline can be used at a concentration of 0.004 to 0.1 mg/ml (e.g., 0.008 to 0.05 mg/ml, or about 0.02 mg/ml). The antibiotics can be present for the whole period of the culture or for a portion of the culture period.

Mycoplasma contamination can be assayed by an agar culture method using a system such as, for example, mycoplasma agar plates that are available from bioMérieux (Marcy l'Etiole, France) or can be prepared in house, or by PCR. The American Type Culture Collection (ATCC, Manassas, Va.) markets a PCR "Mycoplasma Detection Kit". Culture medium containing tylosin (0.06 mg/ml), gentamicin (0.1 mg/ml), ciprofloxacine (0.01 mg/ml), alatrofloxacine (1.0 µg/ml), azithromycin (0.01 mg/ml), and tetracycline (0.02 mg/ml) is particularly useful for preventing mycoplasma contamination. Another agent that can be useful in preventing mycoplasma contamination is a derivative of 4-oxo-quinoline-3-carboxylic acid (OQCA), which is commercially available as, for example, "Mycoplasma Removal Agent" from ICN Pharmaceuticals, Inc. (Costa Mesa, Calif.). This agent typically is used at a concentration of 0.1 to 2.5 mg/ml (e.g., 0.2 to 2.0 mg/ml, or 0.5 mg/ml). The antibiotic mixture or other agents can be present in the fibroblast cultures for the first two weeks after initiation. After a suitable time in culture (e.g., two weeks), antibiotic containing medium typically is replaced with antibiotic-free medium. Once a sufficient number of cells are present in the culture, they can be tested for mycoplasmal, bacterial and fungal contamination. Only cells with no detectable contamination are useful in methods of the invention.

Culture of UMC in Plasma Clots to Generate Neurons

Plasma clots for use in the methods of invention can be produced by any of a variety of methods known in the art. Plasma can be prepared by, for example, adding sodium citrate or heparin to blood recently removed from an appropriate mammalian subject and separating the plasma fraction of the blood from cellular components by centrifugation. The plasma can be obtained in liquid form or, for example, in lyophilized form. If it is obtained in lyophilized form, it is reconstituted prior to use by the addition of deionized water or, for example, tissue culture medium. The plasma can be obtained from the individual to whom the neurons are to be administered (the recipient), i.e., it can be autologous. Alternatively, it can be from one or more individuals of the same species as the recipient, e.g., it can be a pool of plasma samples prepared from a plurality (e.g., 2, 3, 4, 5, 6, 7, 8, 9, 10, 11, 12, 15, 20, 25, 30, 35, 40, 50, 60, 70, 80, 90, 100 or more) human volunteers. In addition, plasma can be isolated from the blood of adult, infant, or fetal blood of one or more individuals of any of a variety of mammalian species, e.g., humans, non-human primates, cows, sheep, horses, goats, pigs, dogs, cats, rabbits, guinea pigs, hamsters, gerbils, rats, or mice. Plasma obtained from these species can be used with UMC from the same species or another species.

The clots can be formed in appropriate vessels (e.g., plastic tissue culture dishes) by mixing the plasma with a source of $Ca^{2+}$ ions (e.g., $CaCl_2$) or thrombin. Even if a method of inducing clotting other than addition of $Ca^{2+}$ ions is used, it is nevertheless required for production of neurons from UMC that there be a relatively high concentration of $Ca^{2+}$ ions in the plasma clot. Thus induction of clotting by the addition of $Ca^{2+}$ ions is preferred. If some other method is used $Ca^{2+}$ ions must be introduced into the clot, e.g., by incubation of the clot in $Ca^{2+}$ contain solution or medium prior to addition of cells to the clots. The concentration of $Ca^{2+}$ in the clots can be about 4 mM–about 18 mM, e.g., about 6 mM–about 17 mM; about 8 mM–16 mM; or about 8 mM–15 mM.

Clotting can be carried out at room temperature or, more rapidly at, for example, 37° C. After formation of the clots sufficient tissue culture medium is added to the vessel containing the clot so as to prevent drying of the clot. Thus the clot can be completely covered with the medium or the medium can be at substantially the same level as the upper surface of the clot.

Tissue culture medium can be any culture medium suitable for the growth of neurons. One such medium is "FGF-DMEM", which contains DMEM that is supplemented with about 2 mM glutamine, about 10 mg/L sodium pyruvate, about 2.5% (v/v) FBS (or any of the human sera disclosed herein), acidic fibroblast growth factor (aFGF; about 5 ng/ml), heparin (about 5 µg/ml), and antibiotics (often called "complete medium"), the concentration of glucose ranging from about 1,000 mg/L to about 4,500 mg/L. Another useful medium is "N medium" containing Neuralbasal medium (Gibco, Carlsbad, Calif.) supplemented with about 2 mM glutamine, B27 Supplement (Gibco; added to Neuralbasal medium in a proportion of about 1:50), epidermal growth factor (EGF; final concentration of about 20 ng/ml), R3 long form insulin-like growth factor (R3 IGF; final concentration of about 25 ng/ml), basic fibroblast growth factor (bFGF; final concentration of about 10 ng/ml), and leukemia inhibitory factor (LIF; final concentration of about 10 ng/ml). If desired, the N-2 Supplement (Gibco) can be used instead of the B27 Supplement. U.S. Pat. No. 6,736,238 (whose disclosure is incorporated herein by reference in its entirety) describes various media suitable for the in vitro growth of neurons.

Culture media for growing neurons can be supplemented with one or more growth factors, e.g., acidic fibroblast growth factor (FGF; aFGF) , basic FGF (bFGF), insulin-like growth factor 1 (IGF-1), long form insulin-like growth factor (R3 IGF), epidermal growth factor (EGF), long form EGF, insulin-like growth factor (IGF), platelet derived growth factor (PDGF), nerve growth factor (NGF), transforming growth factor (TGF) family members (e.g., TGFβ), bone morphogenic protein (BMP) family members (e.g., any of BMP 2-8), FGF-7, FGF-9, ciliary neurotrophic factor (CNTF), brain-derived neurotrophic factor (BDNF), neurotrophic factor-3 (NT-3), neurotrophic factor-4 (NT-4), neurotrophic factor-5 (NT-5), glial cell line-derived neurotrophic factor (GNDF), or LIF. those having deletions, additions, or substitutions) of any of the above growth factors that have at least the 50% of the activity of the full-length wild-type growth factors can also be used for any of the purposes of the invention for which the full-length wild-type growth factors can be used. Also useful are compounds that have been shown to enhance the neuron growth-promoting activity of growth factors; such compounds are described in U.S. Pat. No. 6,172,086, whose disclosure is incorporated herein by reference in its entirety. Moreover, amino acids required for, or that enhance, neuron growth can be added to culture medium for growing neurons, e.g., L-carnitine, L-proline, L-alanine, L-asparagine, and L-cysteine. Other additives include thyroid hormone, vitamin E, ethanolamine, insulin, transferrin, superoxide dismutase, linoleic acid, corticosterone, retinyl acetate, progesterone, and putrescine.

UMC, cell populations containing UMC, or fragments of, or minced, tissue containing UMC are applied to the surface of the clot. The cells, minced tissue, or tissue fragments can be added to culture medium above the clot and allowed to settle by the action of gravity onto the surface of the clot. Alternatively, the level of medium can be adjusted so as to be at the same level as, or at a level a little lower than, that of the upper surface of the clot. The UMC or tissue fragments can then be applied to the surface of the clot and incubated for a sufficient time (e.g., at 37° C.) to allow adherence of the cells or tissue fragments to the surface of the clot. Once adherence has occurred, additional medium can be added so as to completely cover the body of the clot. What is important is that at all times there be sufficient culture medium in the tissue culture vessel to prevent drying of the plasma clot. It is understood that, rather than contacting cells, minced tissue, or tissue fragments with the surface of a plasma clot, the cells, minced tissue, or tissue fragments can be embedded in the plasma clot. Thus they can inserted into the after formation, or they can be added to plasma used to make the clot prior to formation of the clot.

After application of the cells, minced tissue, or tissue fragments to the clots, the culture vessel is incubated under standard tissue culture conditions, e.g., about 37° C. (e.g., 35° C., 36° C., or 37° C.) in an atmosphere of about 5% to about 10% $CO_2$ (e.g., about 5% to about 6.5% $CO_2$) and about 85% to about 98% humidity. Cell growth and morphology can be monitored with an overhead microscope.

Neurons are readily identified by those skilled in the art and are characterized by the presence of an axon and/or a plurality of dendritic processes. Naturally, the frequency of media changes and cell passaging will depend on the rate of cell division in the cultures. This factor will vary according to, for example, the culture medium used, the species of the UMC, and whether growth enhancing factors are used in the cultures or not. Those skilled in the art will be able to establish workable conditions for cultures of interest.

The neurons can be passaged by cutting a clot into smaller fragments and embedding the fragments in, or placing them on the surface of, fresh plasma clots. The neurons and UMC migrate out of the clot fragments into the new clot upon further culture. The neurons migrate into the new clot earlier than the UMC and this factor provides a method of enriching for neurons in clots. Thus, for example, after a culture of a new clot having embedded within it, or attached to its surface, a clot fragment containing both neurons and UMC for a long enough period to allow migration into the body the new clot of a relatively large number of neurons but not long enough for migration into body of the new clot of a substantial number of UMC, either the clot fragment may be removed or the new clot can be cut into small fragments which are in turn embedded into tertiary new clots. Such a process can be repeated as frequently as desired, i.e., until a cell population containing a desired proportion of neurons is obtained.

Alternatively, the cells in the clots can be passaged by dissolving the clots (see below) and collecting the cells from the dissolved clots. These cells can then be added to the surfaces of fresh clots in the essentially the same manner described above for culture initiation.

Cells can be harvested from plasma clots by addition of enzymes such as trypsin, streptokinase, or plasminogen to the cultures and incubating them at room temperature or 37° C.

After harvesting of the cells from the clots, they can be further cultured in serum/plasma-free medium for at least an additional 4 hours (e.g., overnight or about 18 hours). Incubation of the cells in serum-free medium can substantially remove proteins derived from the serum (e.g., FBS) added to the culture medium, which if present in a composition injected into a subject, could elicit an undesirable immune response. Serum-free medium can contain, for example, glucose DMEM supplemented with about 2 mM glutamine, with or without about 110 mg/L sodium pyruvate, wherein the concentration of glucose can range from approximately 1,000 mg/L to about 4,500 mg/L. A glucose concentration of approximately 4,500 mg/L is particularly useful. The serum-free medium also can contain one or more antibiotics such as those described above.

Any of the cell populations (e.g., UMC, UMC-containing cells, neurons, or neuron-containing cells) can be frozen and stored frozen in any medium suitable for freezing such cell types (e.g., any commercially available freezing medium) and stored, for example, in a freezer at about −80° C. or in liquid $N_2$. It is not necessary that cells be harvested from plasma clots prior to freezing; the clot containing the cells can be frozen in a freezing medium. A medium consisting of about 70% (v/v) culture medium, about 20% (v/v) FBS and about 10% (v/v) dimethylsulfoxide (DMSO) is particularly useful for freezing any of the cell types disclosed herein. The FBS can be replaced with, for example, Krebs Ringer containing 5% dextrose, and the DMSO also can be replaced with glycerol, for example. Thawed cells can be used to initiate secondary cultures for the preparation of additional suspensions for later use in the same subject, thus avoiding the inconvenience of obtaining a second specimen.

Neurons and Compositions Containing Neurons

The invention also provides an isolated neuron generated from UMC by the above-described plasma clot method and a composition containing a population of cells that includes a plurality of the neurons generated from UMC by the method. In these cell populations the neurons are preferably at least 5% (e.g., at least: 5%; 7%; 9%; 10%; 12%; 15%; 18%; 20%; 30%; 35%; 40%; 45%; 50%; 55%; 60%; 65%; 70%; 75%; 80%; 85%; 90%; 99%; 99.5%; 99.8%; or 100%) of the cell population. Other cells in the cell populations can be, without limitation, one or more of the following cell types: UMC, fibroblasts, keratinocytes, adipocytes, preadipocytes, melanocytes, skin Langerhans cells, or endothelial cells. In one embodiment the compositions are substantially free of fibroblasts, keratinocytes, adipocytes, preadipocytes, melanocytes, skin Langerhans cells, and endothelial cells; they can also be substantially free of UMC.

In one embodiment, both the neurons and compositions are substantially free of culture medium xenogeneic or allogeneic serum-derived proteins. As used herein, cells that are "substantially free of culture medium xenogeneic or allogeneic serum-derived proteins" are cells in which the fluid surrounding the cells contains less than 0.1% (e.g., less than 0.05%, less than 0.01%, less than 0.005%, or less than 0.001%) of xenogeneic or allogeneic serum contained in tissue culture medium in which the cells were previously cultured. Similarly, a composition that is "substantially free of culture medium xenogeneic or alloegeneic serum-derived proteins" is a composition in which fluid surrounding the cells in the composition contains less than 0.1% (e.g., less than 0.05%, less than 0.01%, less than 0.005%, or less than 0.001%) of xenogeneic or allogeneic serum contained in tissue culture medium in which the cells were previously cultured.

To obtain cells that are substantially free of allogeneic or xenogeneic culture medium serum-derived proteins, cultured cells can be expanded in medium that does not contain allogeneic or xenogneic serum, i.e., in serum free or in autologous serum-containing medium. Alternatively, cells can be cultured first in medium that contains allogeneic or xenogeneic serum (e.g., 0.1% to 20% serum), and subsequently cultured in serum-free medium. The presence of potentially immunogenic serum-derived proteins in a cell suspension is thus avoided by these methods.

A pharmaceutically acceptable carrier e.g., normal saline, excipient, or stabilizer can be added to the cells before they are administered to a subject. The phrase "pharmaceutically acceptable" refers to molecular entities and compositions that, at the concentration used, are not deleterious to cells, are physiologically tolerable, and typically do not produce an allergic or similar untoward reaction, such as gastric upset, dizziness and the like, when administered to a human. A wide variety of pharmaceutically acceptable carriers, excipients or stabilizers are known in the art [Remington's Pharmaceutical Sciences, 16th Edition, Osol, A. Ed. 1980]. Acceptable carriers, excipients, or stabilizers include: buffers, such as phosphate, citrate, and other non-toxic organic acids; antioxidants such ascorbic acid; low molecular weight (less than 10 residues) polypeptides; proteins such as serum albumin, gelatin or immunoglobulins; hydrophilic polymers such polyvinylpyrrolidone; amino acids such as glycine, glutamine, asparagine, arginine, or lysine; monosaccharides, disaccharides, and other carbohydrates including glucose, mannose, or dextrans; chelating agents such as EDTA; sugar alcohols such as mannitol, or sorbitol; salt-forming counterions such as sodium; and/or nonionic surfactants such as Tween, Pluronics, or PEG.

Alternatively, if the cells are not to be administered immediately, they can be incubated on ice at about 4° C. for up to 24–48 hours post-harvest. For such incubation, the cells can be suspended in a physiological solution that has an appropriate osmolarity and has been tested for pyrogen and endotoxin levels. Such a solution typically does not contain phenol red pH indicator, and any serum preferably is the subject's serum (i.e., autologous serum) rather than fetal bovine serum (FBS) or another xenogeneic serum (e.g., horse serum or goat serum). Cells can be suspended in, for example, Krebs-Ringer solution containing 5% dextrose, DMEM without phenol red, or any other physiological solution. The cells can be aspirated and administered to a subject in the incubation medium. The volume of saline or incubation medium in which the cells are suspended typically is related to factors such as the number of cells to be injected and the extent of the damage due to tissue degeneration or defect.

Biodegradable Acellular Matrices

Compositions that contain the neurons of the invention can also include biodegradable acellular matrix components. An acellular matrix component generally fulfils a structural role. For example, it may fill in a defect, hole, space or cavity in tissue and provide an environment in which injected or implanted cells can adhere to the matrix or surrounding tissue and grow and produce structural and other factors (e.g., chemotactic factors) resulting from the growth of new tissue. In many instances, the gap-filling function of the matrix is temporary and only lasts until the implanted and/or host cells migrate into the area and form new tissue. Preferably the acellular matrix is biodegradable. The matrix is preferably a solid or semi-solid substance that is insoluble under physiological conditions. Such compositions are suitable for injection or implantation into a subject to repair tissue that has degenerated. The term "biodegradable" as used herein denotes a composition that is not biologically harmful and can be chemically degraded or decomposed by natural effectors (e.g., weather, soil bacteria, plants, or animals). Examples of matrices that can be used in the present invention include, without limitation, acellular matrices containing autologous and non-autologous proteins, and acellular matrices containing biodegradable polymers.

Any of a number of biodegradable acellular matrices containing non-autologous proteins can be used in the compositions provided herein. Examples of biodegradable acellular matrices include matrices containing any type of collagen (e.g., bovine, porcine, human, or bio-engineered collagen), or any type of collagen with glycosaminoglycans (GAG) cross-linked with, for example, glutaraldehyde. Matrices containing collagen include, without limitation, absorbable collagen sponges, collagen membranes, and bone spongiosa. Useful types of collagen include, for example, bovine collagen (e.g., ZYDERM® and ZYPLAST®, commercially available from McGhan Medical Corporation, Santa Barbara, Calif.), porcine collagen, human cadaver collagen (e.g., FASCIAN™ (Fascia Biosystems, LLC, Beverly Hills, Calif.), CYMETRA™ (LifeCell Corp., Branchburg, N.J.), or DERMALOGEN™ (formerly produced by the Collagenesis Corp.), bioengineered collagen (e.g., FORTAPERM™, available from Organogenesis, Inc., Canton, Mass.), and autologous human collagen (AUTOLOGEN®, see below). FASCIAN™ can be particularly useful. This product is available in five different particle sizes, any of which can be used in compositions and methods described herein. Particles that are 0.25 mm in size can be particularly useful. Another biopolymer useful for such matrices is fibrin. Of interest for the purposes of the invention are plasma clots of the type used to produce neurons from UMC (see above). Indeed, in certain embodiments it will not be necessary to extract the neurons from the plasma clot used to produce them. The clot, optionally cut to an appropriate size and shape, can be implanted directly into, or grafted directly to, a damaged or defective neural tissue.

Absorbable collagen sponges can be purchased from, for example, Sulzer Calcitek, Inc. (Carlsbad, Calif.). These collagen sponge dressings, sold under the names COLLATAPE®, COLLACOTE®, and COLLAPLUG®, are made from cross-linked collagen extracted from bovine deep flexor (Achilles) tendon, and GAG. These products are soft, pliable, nonfriable, and non-pyrogenic. Greater than 90% of a collagen sponge typically consists of open pores.

Biodegradable acellular matrices can contain collagen (e.g., bovine or porcine collagen type I) formed into, for example, a thin membrane. One such membrane is manufactured by Sulzer Calcitek and is marketed as BIOMEND™. Another such membranous matrix is marketed as BIO-GIDE® by Geistlich Söhne AG (Wolhusen, Switzerland), and is made of porcine type I and type III collagen. BIO-GIDE® has a bilayer structure, with one surface that is porous and allows the ingrowth of cells, and a second surface that is dense and prevents the ingrowth of fibrous tissue.

Other suitable matrices containing collagen include COLLAGRAFT®, manufactured by NeuCell, Inc. (Campbell, Calif.), and OSTEOSET® calcium sulfate alpha hemi-hydrate pellets sold by Wright Medical Technology (Arlington, Tenn.).

Biodegradable acellular matrices also can be made from bone spongiosa formed into granules or blocks. This material consists of animal (e.g., human, non-human primate, bovine, sheep, pig, or goat) bone from which substantially all organic material (e.g., proteins, lipids, nucleic acids, carbohydrates, and small organic molecules such as vitamins and non-protein hormones) has been removed. This type of matrix is referred to herein as an "anorganic matrix". One such matrix, which is marketed as BIO-OSS® spongiosa granules and BIO-OSS® blocks, is manufactured by Geistlich Söhne AG. This company also manufactures a block-type matrix (BIO-OSS® collagen) that contains anorganic bone and additionally contains approximately 10% collagen fibers by weight.

Other useful biodegradable acellular matrices can contain gelatin, cat gut, demineralized bone, anorganic bone, coral, or hydroxyapatite, or mixtures of these substances. A matrix made from demineralized human bone, for example, is formed into small blocks and marketed as DYNAGRAFT® by GenSci Regeneration Laboratories, Inc. (Toronto, Ontario, Canada), TUTOPLAST® by Tutogen Medical, Inc. (Clifton, N.J.), or GRAFTON® Demineralized Bone Matrix by Osteotech, Inc. (Eatontown, N.J.). Demineralized bone can be combined with, for example, collagen to produce a matrix in the form of a sponge, block, or membrane. Biodegradable matrices can contain glycosaminoglycans such as mucopolysaccharide or hyaluronic acid.

Particularly useful for the purposes of the invention are biopolymer (e.g., collagen of any of the types disclosed herein or fibrin) gels formed into the shape of small rods. In these rods the biopolymer fibrils are oriented in a longitudinal (axial) direction by means of a magnetic field. Such rods containing neurons, and optionally other cells (such as Schwann cells), can be used to bridge the gap between the severed ends of, e.g., a peripheral nerve. The longitudinally aligned fibrils within the rod serve to guide neural growth across the gap between the severed nerve endings and thereby promote regeneration of the original neural connection. These biopolymer rods and methods of making them are described in greater detail in U.S. Pat. No. 6,057,137, whose disclosure is incorporated herein by reference in its entirety.

In addition, synthetic polymers made from one or more monomers can be used to make biodegradable acellular matrices that are useful herein. Such synthetic polymers include, for example poly(glycolic acid), poly(lactic acid), and poly(glycolic acid)-poly(lactic acid). Synthetic polymers also can be combined with any of the above-mentioned substances to form matrices. Different polymers forming a single matrix can be in separate compartments or layers. For example, W. L. Gore & Associates, Inc. (Flagstaff, Ariz.) manufactures a porous biodegradable acellular matrix (GORE RESOLUT XT Regenerative Material). This matrix is composed of a synthetic bioabsorbable glycolide and trimethylene carbonate copolymer fiber into which cells can migrate, attached to an occlusive membrane that is composed of a synthetic bioabsorbable glycolide and lactide copolymer that does not permit ingrowth of cells. Other examples of suitable biodegradable matrices can be found in U.S. Pat. No. 5,885,829, for example.

Of interest for the purposes of the invention are electrically conducting biopolymers such as polypyrroles, polyanilines, polythiophenes, and derivatives of these polymers. Examples of such derivatives include 3-substituted polyanilines, polypyrroles and polythiophenes, e.g., alkyl substituted derivatives. Matrices can be constructed from these polymers or the polymers can be coated onto any of the other biodegradable acellular matrix materials disclosed herein. The usefulness of such matrices for the instant invention derives from the finding that electrical charges enhance neurite extension and nerve regeneration. The nerve growth enhancing properties of these matrices can be further enhanced by the application, either in vivo or in vitro, of a voltage or electrical current to the matrices with neurons attached prior to placement in a subject. These electrically conducting polymers and their use are described in greater detail in U.S. Pat. No. 6,095,148, whose disclosure is incorporated herein by reference in its entirety.

The ability of cells to attach to the biodegradable acellular matrices can be enhanced by coating the matrices with one or more attachment molecules known in the art. These include natural molecules (e.g., extracellular matrix factors such as laminin and fibronectin) and synthetic molecules (e.g., peptides containing the binding sites of fibronectin and/or laminin). Example of useful agents are, without limitation, basement membrane components, gelatin, gum Arabic, collagen types I–XII, fibronectin, laminin, thrombospondin, entactin, proteoglycans, glycosaminoglycans, and mixtures thereof. Other appropriate attachment molecules include simple carbohydrates, complex carbohydrates, asialoglycoproteins, lectins, growth factors, low density lipoproteins, heparin, poly-lysine, poly-ornithine, thrombin, vitronectin, and fibrinogen. Synthetic molecules include peptides made using conventional methods to incorporate one or more binding sites such as amino acid sequences RGD (SEQ ID NO:1; from fibronectin), LIGRKKT (SEQ ID NO:2; from fibronectin) and YIGSR (SEQ ID NO3; from laminin). Use of attachment molecules and methods for linking them to biodegradable acellular matrices are described in U.S. Pat. No. 6,095,148.

After a biodegradable acellular matrix has been selected, a concentrated suspension of cells (e.g., a suspension containing neurons produced from UMC as described above) can be evenly distributed on the surface of the matrix. A concentrated suspension typically is used in order to avoid exceeding the capacity of the matrix to absorb the liquid suspension. For example, a cell suspension applied to a GORE RESOLUT XT matrix generally can have a volume between about 94 µl and about 125 µl and contain between about $2.0 \times 10^6$ cells and about $4.0 \times 10^6$ cells per square centimeter of matrix. Cells can be allowed to attach to the matrix without further addition of media. Incubation of the cells with the matrix can be at, for example, about 37° C. for about 1–2 hours. Cells typically are attached to and evenly distributed throughout the matrix material after about sixty minutes of incubation. At this time, the culture vessels containing the cell-loaded matrices can be supplemented with additional growth medium, and cells can be cultured in the matrix for about 3 to 4 days. Because the cells are added to the matrix at high density so as to substantially fill the space within the matrix, little or no proliferation occurs during the 3–4 day culture period. Indeed, significant cell proliferation typically is undesirable during this period because dividing cells can secrete enzymes (e.g., collagenase) that can degrade or partially degrade the matrices.

The matrix with the cells attached is typically washed (e.g., at least 3 washes of 10 minutes each) with, for example, saline or medium that is free of serum and phenol red, in order to substantially remove immunogenic proteins (e.g., culture medium serum-derived proteins if medium containing non-autologous serum was used for the matrix seeding step) that could elicit an immune response when administered to a subject. Fresh PBS can be used for each wash. The matrix then can be incubated (e.g., 2 hour-long incubations) in fresh PBS or serum-free culture medium prior to use. After incubation, the matrix containing the cells can be placed at the area of tissue degeneration or defect.

For collagen sponge matrices (e.g., COLLACOTE®), approximately $1.5 \times 10^6$ to $2.0 \times 10^6$ cells (or more as needed) in approximately 1.5 ml of growth medium can be seeded onto a 2 cm by 4 cm thin (approximately 2.5 to 3.0 mm in thickness) sponge. The sponge then can be incubated at 37° C. for about 1–2 hours without further addition of medium to allow substantially all cells to adhere to the matrix material. After cell adherence, additional growth medium can be added to the matrix and cell composition, which then can be incubated at 37° C. for 3–4 days with a daily change of medium. If medium containing non-autologous serum was used for the cell seeding step, the composition can be removed from growth medium containing such serum and washed repeatedly (e.g., 3 times or more) with PBS. After each addition of PBS, the matrix can be incubated for 10–20 minutes prior to discarding the PBS. After the final wash, the composition can either be administered immediately to a subject, or can be transferred to a shipping vial containing a physiological solution (e.g., Kreb's Ringer solution) and incubated at about 4° C. for up to about 24–48 hours.

For a membranous matrix (e.g. BIOMEND™), approximately $1.5 \times 10^6$ to $2 \times 10^6$ cells (or more as needed) in about 100 µl of growth medium can be seeded onto a 15 mm×20 mm thin (approximately 0.5 to 1.0 mm in thickness) membrane. The membrane can be incubated at 37° C. for about 30-60 minutes without further addition of medium to allow substantially all of the cells to adhere to the matrix material. After cell adherence, additional growth medium can be added to the matrix and cell composition, which then can be incubated at 37° C. for 2–3 days with a daily change of medium. The cells typically are added to the matrix at high density (see above) so as to substantially fill the space within the matrix available for cells. Washing of the composition and either immediate use or incubation can be as described above for the sponge matrices.

In the case of a block matrix such as the above described anorganic matrix (e.g., the BIO-OSS® block) or a demineralized bone matrix (e.g., the DYNAGRAFT™ matrix), approximately $1.5 \times 10^6$ to $2.0 \times 10^6$ cells (or more as needed) in approximately 100 to 150 μl of growth medium can be seeded into a 1 cm×1 cm×2 cm cubic block of matrix material. Cells typically are seeded slowly onto one face of the block face. Once the medium and cells have been absorbed into the block, another face of the block can be seeded in a similar fashion. The procedure can be repeated until all faces of the block have been seeded and the block is fully saturated with medium. Care should be taken to avoid adding excess medium and thereby causing leakage of medium and cells from the block. The composition then can be incubated at 37° C. for about 60–120 minutes without further addition of medium to allow substantially all the cells to adhere to the matrix material. After cell adherence, additional growth medium can be added to the matrix and cell composition, which then can be incubated at 37° C. for 2–3 days with a daily change of medium. The cells typically are added to the matrix at high density (see above) so as to substantially fill the space within the matrix available for cells with the same result described above. Washing of the composition and either immediate use or incubation are as described above for the sponge matrices.

Compositions containing the neurons of the invention and a small particle biodegradable matrix (e.g., FASCIAN™, CYMETRA™, or DERMALOGEN™) can be prepared by mixing the components by, for example, passing them back and forth between two syringes that are connected via a luer lock. FASCIAN™, for example, is typically available in syringes (e.g., 3 cc syringes) at 80 mg/syringe. FASCIAN™ particles can be washed directly in the syringe prior to use by taking up a small volume (e.g., 1.5 ml) of a wash buffer (e.g., isotonic saline or Kreb's Ringers solution containing dextrose) into the syringe, connecting the first syringe to a second syringe via a luer lock, and passing the particles and wash solution back and forth between the two syringes several times. To separate the particles from the wash solution, the mixture can be transferred to a sterile tube and the FASCIAN™ particles allowed to settle. The solution can be removed (e.g., decanted or aspirated), and the washing process can be repeated as desired by taking up the particles into a fresh syringe (e.g., through an 18 gauge or 20 gauge needle).

When the particles are suitably washed, they can be mixed with cells using the same procedure as for washing. Cells (e.g., $1.5 \times 10^6$ to $2 \times 10^6$ cells) can be suspended in solution (e.g., 1.5 ml of Kreb's Ringers solution with 5% dextrose) and taken up into a syringe. The syringe containing the cells can be connected to a syringe containing the filler particles via a luer lock, and the two components can be mixed by passing them back and forth between the syringes. The mixture then can be transferred to a T-25 tissue culture flask or to a tissue culture dish or a tube so that the cells can attach to the filler particles. Alternatively, the mixture can remain in the syringes while attachment occurs, although this may be more detrimental to the cells. The mixture can be incubated over night and then transferred to a container (e.g., a vial or a tube) for delivery to a clinician, or transferred to a syringe for administration to a subject. A container to be delivered to a clinician can be kept on ice during delivery. When such small particle acellular biodegradable matrices are used, a suspension of the cell-containing particles can optionally be injected rather than implanted into an area of tissue degeneration or defect.

It is understood that compositions of the invention can contain, in addition to cells and a pharmaceutically acceptable carrier, and/or a biodegradable acellular matrix (see below), and/or a biodegradable acellular filler (see below), any one or more of the nerve cell growth factors listed above.

The invention also provides methods for making compositions that contain both neurons of the invention and matrix components. These methods typically involve providing a population of cells that include a plurality of neurons, providing a biodegradable acellular matrix, incubating the biodegradable acellular matrix with the population of cells such that the cells integrate on and within the matrix, thus forming a composition for repairing damaged or defective neural tissue.

Biodegradable Acellular Filler Materials

Compositions of the invention can contain the neurons of the invention together with one or more biodegradable acellular injectable filler materials (i.e., bulking agents). The compositions are suitable for injection into a subject in order to repair tissue that has degenerated. A filler material generally fulfils a structural function. For example, it may fill in a defect, hole, space or cavity in tissue and provide an environment in which injected cells can adhere to the surrounding tissue and grow and produce structural and other factors (e.g., chemotactic factors) resulting from the growth of new tissue. In many instances, the gap-filling function of the filler is temporary and only lasts until the implanted and/or host cells migrate into the area and form new tissue. Preferably the filler is biodegradable. Fillers are typically provided and used as a viscous solution or suspension. Fillers can be combined with a cell population that includes neurons of the invention.

Numerous types of biodegradable, acellular injectable fillers can be used in the compositions of the invention. A filler can consist of autologous proteins, including any type of collagen obtained from a subject. An example of such a filler is Autologen®, formerly produced by Collagenesis Corp. (Beverly, Mass.). Autologen® is a dispersion of autologous dermal collagen fibers from a subject, and therefore does not elicit even a minimal immune response when readministered to the subject with cells such as UMC and, optionally, fibroblasts. In order to obtain Autologen®, a specimen of tissue (e.g., dermis, placenta, or umbilical cord) is obtained from a subject and forwarded to Collagenesis Corp., where it is processed into a collagen-rich dispersion. Approximately one and a half square inches of dermal tissue can yield one cubic centimeter (cc) of Autologen®. The concentration of Autologen® can be adjusted depending upon the amount required to correct defects or augment tissue within the subject. The concentration of Autologen® in the dispersion can be, for example, at least about 25 mg/L (e.g., at least about 30 mg/L, at least about 40 mg/L, at least about 50 mg/L, or at least about 100 mg/L).

An acellular injectable filler material can also contain non-autologous proteins, including any type of collagen. Numerous collagen products are commercially available and can be used in compositions of the invention. Human collagen products also are commercially available. Examples of commercially available collagen include, without limitation, bovine collagen, e.g., reconstituted bovine collagen products such as Zyderm® and Zyplast®, which contain reconstituted bovine collagen fibers that are cross-linked with glutaraldehyde and suspended in phosphate buffered physiological saline with 0.3% lidocaine. These products are produced by McGhan Medical Corporation of Santa Barbara, Calif. Porcine collagen products also are commercially available. Collagens useful in the invention can be isolated from tissues of appropriate species, or they can be made as recombinant proteins. Recombinant proteins can have amino acid sequences identical to those of the naturally occurring proteins, or they can have amino acid sequences containing amino acid substitutions, deletions, or insertions that improve the function of the proteins.

Other examples of useful filler materials include, but are not limited to, solubilized gelatin, polyglycolic acid (e.g., solubilized polyglycolic acid or particles of polyglycolic acid), or cat gut sutures. A particular gelatin matrix implant, for example, is sold under the mark Fibril®. This filler contains equal volumes of (1) a mixture of porcine gelatin powder and o-aminocaproic acid dispersed in a 0.9% (by volume) sodium chloride solution, and (2) an aliquot of plasma from the subject. Other substances useful as fillers include hyaluron, hyaluronic acid, restalyn, and parleane.

The invention also provides methods for making compositions that contain neurons of the invention and biodegradable acellular fillers. These methods typically involve providing a population of cells that include neurons of the invention that are substantially free of immunogenic proteins (e.g., culture medium serum-derived proteins), providing one or more biodegradable acellular filler materials, and combining the filler with the population of cells.

Methods of Using the Neurons of the Invention

The neurons and compositions of the invention can be used in vitro or in vivo. In vitro uses of the neurons and compositions containing the neurons include their use as targets for in vitro screening or testing of compounds of interest for, e.g., neuron growth-promoting activity or neurotoxic activity. They can also be used for both in vitro and in vivo studies of basic neurobiology.

The neurons are particularly useful for the treatment of any of a variety of neurological conditions (see above). The neurons can be administered by injection, implantation, or grafting. They can be implanted during surgery, for example, to remove a tumor at the site of tumor excision. Thus, for example, a composition containing the neurons of the invention (see above) in a pharmaceutically acceptable carrier and/or a biodegradable acellular filler (see above) can be injected into a CNS region (e.g., brain ventricle or spinal cord) of interest. Alternatively, neurons attached to and/or incorporated into a biodegradable acellular matrix (see above) can be implanted into, or grafted to, a damaged or defective CNS tissue (brain or spinal cord) or a peripheral nerve.

Administrations can be single or multiple. Thus, they can be made one, two, three, four, five, six, seven, eight, nine, ten, 11, 12, 13, 14, 15, 17, 20, 25, 30, 35, 40, 45, 50, 60, 70, 80, 100, 150, 200, 250, 300, 350, 400, 450, 500, 700, 1000, or more times. Where a plurality of administrations is made, the administrations can separated by any appropriate time period, e.g., 30 seconds, one minute, two minutes, three minutes, four minutes, five minutes, 10 minutes, 20 minutes, 30 minutes, 45 minutes, 1 hour, two hours, three hours, four hours, five hours, eight hours, 12 hours, 18 hours, 24 hours, two days, three days, four days, a week, two weeks, three weeks, a month, two months, three months, four months, five months, six months, eight months, ten months, a year, 18 months, two years, three years, four years, five years, six years, eight years, ten years, 12 years, 15 years, 18 years, 20 years, 25 years, 30 years, 40 years, 50 year an even longer time period.

One or more growth factors can also be administered to recipients of the neurons of the invention. These factors include any of those listed above. It is understood that relevant growth factors may act directly to promote the growth of implanted or grafted neurons or may facilitate tissue repair indirectly by acting on other cells e.g., by enhancing angiogenesis. The growth factors can be administered to a subject as components of the compositions containing the neurons. Alternatively, they can be administered separately and either simultaneously or at a different time. Moreover they can be administered at the same site as the cellular composition or at a different site. They can be administered systemically or locally, e.g., orally, transdermally, intrarectally, intravaginally, intranasally, intragastrically, intratracheally, or intrapulmonarily, or injected (or infused) intravenously, subcutaneously, intramuscularly, or intraperitoneally. Frequencies of administration are as for the cellular compositions (see above).

A growth factor can be administered in the form of the growth factor itself. Alternatively, it can be delivered bound to, or encapsulated within, a solid substrate that acts as reservoir or depot of the growth factor. The solid substrate can be an object or a plurality of objects (configured, for example, as particles or threads). The growth factor is gradually released from the solid substrate into its environment. Where a solid substrate in the form of beads, the beads generally have an approximately spherical shape with a diameter of approximately 0.005–2.0 mm. Where the solid substrate is in the form of threads, the threads are generally 0.01–1.0 mm in diameter. The threads can be folded into a meshwork or cut into small pieces (of approximately 5–10 mm) prior to gel formation. Where the composition containing neurons also contains a biodegradable acellular matrix, it is understood that the matrix can, if desired, also function as a solid substrate for slow release of growth factors. Substances from which the solid substrates can be manufactured include collagen, gelatin, ethylene-vinyl acetate, polylactide/glycolic acid co-polymer, fibrin, sucrose octasulfate, dextran, polyethylene glycol, an alginate, polyacrylamide, cellulose, latex, polyhydroxyethylmethacrylate, nylon, dacron, polytetrafluoro-ethylene, polyglycolic acid, polylactic acid, polystyrene, polyvinylchloride co-polymer, cat gut, cotton, linen, polyester, and silk.

A solid substrate can have heparin or heparan sulfate proteoglycan bound to it as a means for promoting binding of a heparin-binding growth factor (e.g., bFGF, VEGF, or PDGF) to it. An example of such a solid substrate is beads consisting primarily of agarose with heparin bound to them. The solid substrate can be in a variety of physical forms, e.g., beads, irregular particles, sheets, or threads. When the growth factor is encapsulated in the solid substrate, the growth factor is released gradually over time, e.g., due to enzymes that act on the solid substrate.

Another means by which one or more growth factors can be delivered to a subject is by the administration to the subject of recombinant cells transfected or transformed with one or more expression vectors containing nucleic acid sequences encoding one or more growth factors. The cells can be the neurons themselves or other cell types, e.g., fibroblasts, UMC, keratinocytes, endothelial cells, or lymphoid cells. The same histocompatibility requirements applicable to neurons (see above) are applicable to recombinant cells used to deliver growth factors; the cells will preferably be derived from the recipient, i.e., they will be autologous.

In that the neurons of the invention are derived from UMC, it is understood that all the UMC described herein (e.g., those produced by the method described in Example 1) can be used to treat the same neurological conditions recited here as treatable with the neurons of the invention. Moreover, the UMC can be components of any of the compositions described herein.

The following examples serve to illustrate, not limit, the invention.

EXAMPLES

Example 1

Isolation of Autologous UMC and Fibroblasts

Cells were harvested and enriched in vitro for UMC by initiation of cultures from a skin biopsy obtained from a normal healthy human volunteer as follows. Biopsies of about 10 to about 200 mm$^3$ were obtained from the post auriculum area, and fibroblast tissue culture initiated as described above using DMEM containing 4500 mg/L D-glucose, 2 mM L-glutamine, nonessential amino acids, and 10% FBS. Colonies of non-adherent, actively growing cells were observed after adherent fibroblasts had reached full confluence in passage two or three. This process could be shortened by initiation of the culture in low serum and by the presence of 5 ng/ml aFGF, or by growth of the cells in a plasma clot directly from tissue (see Example 2) with addition of 300 mM $CaCl_2$ to a final concentration of 15 mM. Each colony contained between 2 and about 80 cells that had a cobblestone-like morphology and were actively dividing. The colonies were collected by aspiration of culture medium containing the floating colonies and centrifugation of this medium. The cells pelleted by centrifugation were transferred to new tissue culture vessels by direct seeding in fresh culture medium containing aFGF and heparin (DMEM containing 4500 mg/L D-glucose, 2 mM L-glutamine, 2.5% heat inactivated FBS, 5 ng/mL recombinant human aFGF, and 5 µg/mL heparin). The cell suspension was added to fresh tissue culture flasks, which were incubated at 37° C. Cells were fed twice weekly, and were passaged or differentially trypsinized when confluence was reached (generally within one to two weeks). Colonies of cobblestone-like cells were observed within about 3–6 weeks of initiation of the culture. Isolation of the colonies and culturing in fresh tissue culture vessels caused the cells to become adherent.

Colonies of non-adherent cells also were isolated from human adipose tissue as follows. The tissue was cut into small pieces and all visible membranes were removed. The tissue was placed in culture in DMEM containing 4500 mg/L D-glucose, 2 mM L-glutamine, 2.5% heat inactivated FBS, 1 to 10 ng/mL recombinant human aFGF, and 5 µg/mL heparin. Under these conditions, cobblestone-like cells were actively shed from the adipose tissue, and continued to grow for a prolonged period of time. The pieces of adipose tissue were washed and placed into fresh tissue culture vessels. Within about 2 weeks, UMC were isolated from the tissue by treatment with collagenase IV for about 5–15 minutes at 37° C. New cells from the adipose tissue remained actively growing in culture for over a year, until the cultures were terminated. Once the cultures were fully grown, clusters of non-adherent cells were observed. When these cells were reseeded in fresh tissue culture flasks, the same type of cells were observed to be actively growing.

In the presence of aFGF, cells in the cultures from both skin and adipose tissue were morphologically homogeneous in appearance and had a cobblestone-like morphology. Upon removal of aFGF from the culture medium, however, most of the cells fully differentiated into adherent fibroblasts. The cobblestone-like non-adherent cells also were observed in cultures initiated from bone marrow, using a method described by Marko et al. (supra). Thus, it seems that at least the non-adherent epithelioid-like cells harvested from fibroblast cultures established from dermis or from cultures of adipose tissue or bone marrow are indeed UMC.

Example 2

Differentiation of UMC into Neurons

In preliminary experiments, clots prepared from bovine plasma were found to be as efficient at supporting cell growth as those produced from fetal bovine plasma. The presence of higher concentration of $Ca^{2+}$ than normally present in culture medium (i.e., about 2 mM) was essential for growth of neurons in the plasma clot UMC cultures. The differentiation, growth and migration of nerve cells in plasma clots were found to be dependent on the concentration of $Ca^{2+}$ (in the form of $CaCl_2$) used for production of the clots. The optimum concentration of $CaCl_2$ was found to be between about 8 mM and 15 mM.

The following is a description of a typical experiment.

Lyophilized bovine plasma (Sigma Aldrich Co., St. Louis, Mo.; Cat. No. P-4639) was reconstituted with an appropriate volume of tissue culture medium not containing heparin, e.g., DMEM or Neurobasal medium (see above). An appropriate volume of a stock solution of $CaCl_2$ (e.g., 300 mM) was added to a series of plastic tissue culture dishes (one set having a diameter of 30 mm and another set having a diameter of 60 mm) so as to give a final concentration of 15 mM after addition of plasma. Plasma was added to the culture dishes (1 ml to 30 mm dishes and 2 ml to the 60 mm dishes), which were swirled in order to mix the $CaCl_2$ and plasma. Thin clots (less than 1 mm in height) were produced by adding 0.5 to 0.75 ml of plasma to 30 mm dish and 1.0 to about 1.25 ml of plasma to a 60 mm dish; appropriate volumes of $CaCl_2$ solution to give a final concentration of 15 mM were added to the dishes as described above.

The dishes were then incubated at room temperature or 37° C. until the plasma had clotted. Clotting at 37° C., which is faster than at room temperature, takes about 2–3 hours. Approximately 2 ml of tissue culture medium was added to the 30 mm tissue culture dishes and 5 ml to the 60 mm tissue culture dishes. The tissue culture medium was "N medium" (see above). The dishes were then stored in a tissue culture incubator at 37° C. in at atmosphere of 10% $CO_2$ until ready for use. A small quantity (about 5 cells to about $10^5$ cells per clot) of dermal-derived UMC prepared as described in Example 1 was added to each dish and the cells were allowed to settle onto each clot. The tissue culture medium in the culture dishes was changed every 3–4 days; 1.5 ml was added to 30-mm dishes and 3 ml to 60-mm dishes after removal of spent medium. Growth of cells in the clots, which was observed microscopically, continued for approximately one year.

Differentiation of a subpopulation of the UMC in plasma clot into neurons was observed from 2–3 days after initiation of the cultures. In the majority of cultures, small cells with only one axon were the first cells of neuronal morphology to appear. At later stages, cells having a dendritic appearance were visible in the cultures. The majority of UMC-derived neurons grew in the upper part of the clot and cells retaining UMC morphology were close to the bottom of the clot.

When the cells in the clots reached a high density, one or more pieces of the plasma clot was transferred onto a freshly prepared plasma clot. Cells migrated from the transferred piece into the new clot in 18–24 hours. Neurons were the first cells to migrate into the new clot. Plasma clots containing cells were stored in liquid $N_2$ using a standard DMSO-containing freezing medium (see above).

If a thin (less than 1 mm in the vertical dimension) plasma clot was used for neuron outgrowth, cells could be harvested from the clots by treatment with trypsin using standard techniques. Plasminogen (Sigma; Catalog No. P-9156) was used for recovery of neurons from thicker plasma (about 3 mm to about 4 mm in vertical dimension) clots at a concentration of 1 U/ml. Three treatments were required to release the neurons from clots. Cells released by the first two treatments were almost all, if not all, UMC and other contaminating cells. It seems likely that by increasing the concentration of plaminogen, it may be possible to release neurons by one or possibly two treatments.

Growth of neurons in the clots was increased by including the B27 (or N-2) culture additive mixture (Gibco, Carlsbad, Calif.) in the culture medium surrounding the clots. Enhanced growth of human neurons was also observed using aFGF as the only growth factor in the culture medium. However, in parallel experiments performed with UMC prepared from rat skin, a combination of the growth factors (bFGF, long form EGF, LIF, and R3 long form IGF) was required; the presence of these growth factors in addition to aFGF in human cell cultures further increased growth of neurons.

It was also possible to generate neurons in plasma clots using, instead of UMC produced by the method described in Example 1, small pieces (e.g., approximately cuboid fragments with each dimension being about 0.5 to about 5 mm) of both skin and fat tissue. The two tissues were tested in separate experiments. The pieces of tissue were placed directly on the surface of the clots. The level of culture medium in the culture dish was sufficiently high to prevent drying of the clot but sufficiently low to prevent floating of the tissue fragments and to allow their attachment to the surface of the plasma clot. In these cultures, overgrowth by fibroblasts was prevented by using medium with a low serum concentration (i.e., not greater than 2.5%) and the inclusion of human aFGF (5 ng/ml). Basic FGF (bFGF) can also be added to the medium. Within 5–7 days of initiation of these cultures, neurons were observed growing in the clot in the immediate vicinity of the tissue fragments. Tissue (skin or fat) pieces could be removed from the original plasma clot and used to seed new plasmas clots. Neurons recovered from fat tissue differed in morphology from neurons recovered from skin. While those generated from skin were small dendritic cells, those generated from fat were large oligodendritic cells.

After seeding into plasma clots, UMC (also referred to previously as preadipocytes) derived from human and rat bone marrow gave rise to neurons in the plasma clots. These UMC/preadipocytes are described in co-pending U.S. application Ser. No. 10/330,584 whose disclosure is incorporated herein by reference in its entirety. In view of the ability to grow neurons from fragments of skin and fat (see above), it is likely that it would be similarly possible to grow them from either bone marrow cells or bone marrow fragments placed on the surface of plasma clots as was done with the skin and fat fragments.

Once neurons have been produced by the above-described plasma clot methodology, they can be isolated from the clots and grown under standard liquid culture conditions.

A number of embodiments of the invention have been described. Nevertheless, it will be understood that various modifications may be made without departing from the spirit and scope of the invention. Accordingly, other embodiments are within the scope of the following claims.

What is claimed is:

1. A method of producing neurons, the method comprising: incubating a population of mammalian cells in a plasma clot containing about 6 mM to about 18 mM Ca2+,
   wherein the mammalian cells are: (i) human or rat cells; and (ii) skin cells, fat tissue cells, or bone marrow cells, and
   wherein the incubation is carried out in a culture medium comprising one or more additives selected from the group consisting of B27 supplement, epidermal growth factor, R3 long form insulin-like growth factor, basic fibroblast growth factor, and leukemia inhibitory factor, wherein during the incubation neurons appear in the plasma clot.

2. The method of claim 1, wherein population of cells is a population of skin cells.

3. The method of claim 1 wherein the population of cells is a population of fat tissue cells.

4. The method of claim 1, wherein the population of cells is a population of non-adherent derivative cells, the non-adherent derivative cells produced by a process comprising:
   (a) culturing starting cells obtained from a tissue selected from the group consisting of skin, fat, and bone marrow; and
   (b) harvesting the population of non-adherent derivative cells from said culture.

5. The method of claim 4, the process further comprising one or more rounds of derivitization comprising repeating steps (a) and (b) utilizing the harvested population of non-adherent derivative cells from the previous round as the starting cells.

6. The method of claim 5, wherein the one or more additional rounds of derivatization comprises from one to twenty rounds.

7. The method of claim 4, further comprising culturing said non-adherent cells in the presence of acidic fibroblast growth factor.

8. The method of claim 1, further comprising harvesting the population of neurons from the plasma clot.

9. The method of claim 8, further comprising culturing the harvested population of cells in a serum-free culture medium.

10. The method of claim 8, wherein the population of cells is obtained from an individual to whom the neurons are administered.

11. The method of claim 4, wherein said tissue is dermal tissue.

12. The method of claim 4, wherein said tissue is adipose tissue.

13. The method of claim 1, wherein the population of mammalian cells is a population of human cells.

14. The method of claim 1, wherein the population of mammalian cells is a population of rat cells.

* * * * *